United States Patent
Etou et al.

(10) Patent No.: US 12,325,675 B2
(45) Date of Patent: Jun. 10, 2025

(54) DEHYDRATION METHOD FOR FLUORINE-BASED HYDROCARBON COMPOUND

(71) Applicant: DAIKIN INDUSTRIES, LTD., Osaka (JP)

(72) Inventors: Yuusuke Etou, Osaka (JP); Shingo Nakamura, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 529 days.

(21) Appl. No.: 17/824,463

(22) Filed: May 25, 2022

(65) Prior Publication Data

US 2022/0281786 A1 Sep. 8, 2022

Related U.S. Application Data

(63) Continuation of application No. PCT/JP2020/044095, filed on Nov. 26, 2020.

(30) Foreign Application Priority Data

Nov. 28, 2019 (JP) ................. 2019-215296

(51) Int. Cl.
*C07C 17/389* (2006.01)

(52) U.S. Cl.
CPC ................... *C07C 17/389* (2013.01)

(58) Field of Classification Search
CPC ....... C07C 17/389; C07C 19/08; C07C 21/18; C09K 13/08; C09K 5/04; C09K 13/00
See application file for complete search history.

(56) References Cited

U.S. PATENT DOCUMENTS

| | | | |
|---|---|---|---|
| 5,600,040 A * | 2/1997 | Corbin | C07C 17/389 570/179 |
| 2003/0157009 A1 | 8/2003 | Corr et al. | |
| 2004/0242943 A1 | 12/2004 | Kaga et al. | |
| 2005/0065385 A1 | 3/2005 | Kaga et al. | |
| 2006/0185972 A1 | 8/2006 | Balthasart et al. | |
| 2007/0015944 A1 * | 1/2007 | Hoos | B01J 20/20 570/262 |
| 2016/0075927 A1 * | 3/2016 | Fukushima | C09K 5/045 252/68 |

FOREIGN PATENT DOCUMENTS

| | | |
|---|---|---|
| EP | 0 526 002 | 2/1996 |
| JP | 6-107572 | 4/1994 |
| JP | 7-508980 | 10/1995 |
| JP | 8-206494 | 8/1996 |
| JP | 9-510214 | 10/1997 |
| JP | 2003-261476 | 9/2003 |
| JP | 2003-525918 | 9/2003 |
| JP | 2011-083726 | 4/2011 |
| WO | 94/01386 | 1/1994 |
| WO | 95/24370 | 9/1995 |

OTHER PUBLICATIONS

Extended European Search Report issued Dec. 1, 2023 in corresponding European Patent Application No. 20892783.0.
International Search Report issued Jan. 12, 2021 in International (PCT) Application No. PCT/JP2020/044095.

* cited by examiner

*Primary Examiner* — Jafar F Parsa
(74) *Attorney, Agent, or Firm* — Wenderoth, Lind & Ponack, L.L.P.

(57) ABSTRACT

An object of the present disclosure is to provide a method for dehydrating a composition containing a fluorine-based hydrocarbon compound, such as HFC-134a. The dehydration method includes the step of bringing a composition containing a fluorine-based hydrocarbon compound into contact with a zeolite.

8 Claims, No Drawings

DEHYDRATION METHOD FOR FLUORINE-BASED HYDROCARBON COMPOUND

TECHNICAL FIELD

The present disclosure relates to a method for dehydrating a fluorine-based hydrocarbon compound.

BACKGROUND ART

Fluorine-based hydrocarbon compounds such as difluoromethane (HFC-32) are widely used in etching gas in the semiconductor production process.

Fluorine-based hydrocarbon compounds such as HFC-32 have been conventionally subjected to water adsorption by using a zeolite A to dehydrate the compounds (e.g., PTL 1).

CITATION LIST

Patent Literature

PTL 1: U.S. Pat. No. 5,446,710

SUMMARY

The present disclosure includes the following subject matter.

Item 1.

A method for dehydrating a composition containing a fluorine-based hydrocarbon compound,
wherein the fluorine-based hydrocarbon compound is at least one compound selected from the group consisting of 1,1,1,2-tetrafluoroethane (HFC-134a), 1,1,1,2,2-pentafluoroethane (HFC-125), difluoromethane (HFC-32), and 2,3,3,3-tetrafluoropropene (HFO-1234yf),
the method comprising the step of bringing the composition containing the fluorine-based hydrocarbon compound into contact with a zeolite having a ratio of silica to alumina ($SiO_2/Al_2O_3$) of 5 or more.

Advantageous Effects of Invention

The present disclosure provides a method for dehydrating a composition containing a fluorine-based hydrocarbon compound, such as HFC-134a.

DESCRIPTION OF EMBODIMENTS

It is important to remove moisture from etching gas in the semiconductor production process.

The present inventors conducted extensive research and found that in dehydrating a composition containing a fluorine-based hydrocarbon compound, such as HFC-134a, if the composition containing a fluorine-based hydrocarbon compound, such as HFC-134a, is brought into contact with a zeolite having a molar ratio of silica to alumina ($SiO_2/Al_2O_3$) of 5 or more, or brought into contact with chabazite zeolite, the release of the moisture adsorbed by the zeolite from the zeolite is suppressed even after the dehydration treatment time is passed, and moisture is well removed (dehydrated) from the composition containing the fluorine-based hydrocarbon compound, such HFC-134a.

The inventors conducted further research on the basis of this finding and completed the present disclosure.

The present disclosure includes the following embodiments.

(1) The Dehydration Method for a Composition Containing a Fluorine-Based Hydrocarbon Compound The method for dehydrating a composition containing a fluorine-based hydrocarbon compound according to the present disclosure includes the step of bringing the composition containing a fluorine-based hydrocarbon compound into contact with a zeolite having a ratio of silica to alumina ($SiO_2/Al_2O_3$) of 5 or more.

The method for dehydrating a composition containing a fluorine-based hydrocarbon compound according to the present disclosure includes the step of bringing the composition containing a fluorine-based hydrocarbon compound into contact with at least one zeolite selected from the group consisting of chabazite zeolite, mordenite zeolite, beta zeolite, and zeolite Y.

The method for dehydrating a composition containing a fluorine-based hydrocarbon compound according to the present disclosure preferably further includes the step of bringing the composition containing a fluorine-based hydrocarbon compound into contact with the zeolite to remove 1,1,2,2-tetrafluoroethane (HFC-134).

In the method for dehydrating a composition containing a fluorine-based hydrocarbon compound according to the present disclosure, the fluorine-based hydrocarbon compound contains at least one compound selected from the group consisting of 1,1,1,2-tetrafluoroethane (HFC-134a), 1,1,1,2,2-pentafluoroethane (HFC-125), difluoromethane (HFC-32), and 2,3,3,3-tetrafluoropropene (HFO-1234yf).

In the step of the present disclosure, the maximum value of the moisture content in the composition after dehydration is about 10 ppmwt (mass/mass), and the moisture content is preferably less than 3 ppmwt. In the present disclosure, the minimum value of the moisture content in the composition after dehydration is about 0.1 ppmwt.

In the step of the present disclosure, the maximum value of the HFC-134 content in the composition after dehydration is about 10 ppmwt (mass/mass), and the HFC-134 content is preferably less than 3 ppmwt. In the present disclosure, the minimum value of the HFC-134 content in the composition after dehydration is about 0.1 ppmwt.

In the step of the present disclosure, more preferably, the moisture content in the composition after dehydration is less than 3 ppmwt, and the HFC-134 content is less than 3 ppmwt.

In the present disclosure, when the HFC-134 content (ppm) is measured, for example, by performing mass spectrometry based on gas chromatography/mass spectrometry (GC/MS) by using gas chromatography and also performing structural analysis based on an NMR spectrum by NMR, the HFC-134 content is a volume fraction obtained by dividing the HFC-134 content (volume) in the composition containing a fluorine-based hydrocarbon compound by the volume of the composition containing a fluorine-based hydrocarbon compound (i.e., ppmvol (volume/volume)).

The HFC-134 content (ppm) can also be paraphrased as, for example, less than 3 ppmvol.

The method for dehydrating a composition containing a fluorine-based hydrocarbon compound according to the present disclosure has advantages in that when the fluorine-based hydrocarbon compound, such as HFC-134a, is dehydrated, due to the use of a specific zeolite, the release of the moisture adsorbed by the zeolite from the zeolite is suppressed even after time passes, and moisture is thus removed well from the composition containing a fluorine-based hydrocarbon compound, such as HFC-134a, and further that preferably, HFC-134 is removed well from the composition containing a fluorine-based hydrocarbon compound, such as HFC-134a.

(1-1) The Composition Containing a Fluorine-Based Hydrocarbon Compound

Fluorine-based hydrocarbon compounds, such as HFC-134a, are used in etching gas for silicon oxide and related materials in semiconductor production. Fluorine-based hydrocarbon compounds, such as HFC-134a, used in the semiconductor industry must be highly pure. In the semiconductor production process, in particular, the removal of moisture from etching gas is important.

In the method for dehydrating a composition containing a fluorine-based hydrocarbon compound according to the present disclosure, the fluorine-based hydrocarbon compound contains at least one compound selected from the group consisting of HFC-134a, HFC-125, HFC-32, and HFO-1234yf.

Compositions containing a fluorine-based hydrocarbon compound, such as HFC-134a, contain impurities that can be mixed during the production of the fluorine-based hydrocarbon compound, such as HFC-134a. Such impurities include intermediates, isomers, and by-products (e.g., hydrogen fluoride, hydrofluorocarbons, hydrochlorofluorocarbons, chlorofluorocarbons, and fluoroalkenes).

Compositions containing a fluorine-based hydrocarbon compound, such as HFC-134a, contain impurities that can be mixed in the use of the fluorine-based hydrocarbon compound, such as HFC-134a. When a fluorine-based hydrocarbon compound, such as HFC-134a, is used as etching gas for semiconductor production, the impurities can be water, acids such as HF, fluorocarbons, or non-condensed gas ($N_2$, $CO_2$, $CH_4$, $O_2$). When a fluorine-based hydrocarbon compound, such as HFC-134a, is used in refrigerants for refrigerating machines, the impurities can be water.

Impurities for compositions containing a fluorine-based hydrocarbon compound, such as HFC-134a, include 1,1,2,2-tetrafluoroethane (HFC-134) in addition to water.

If a composition containing a fluorine-based hydrocarbon compound, such as HFC-134a, contains impurities such as water or hydrogen fluoride (in particular, when the fluorine-containing compound is chemically unstable due to the presence of a reactive site such as a double bond), transformation of the fluorine-containing compound (e.g., decomposition, polymerization, and isomerization) can occur, which may create a vicious circle that further decreases purity.

In the present disclosure, impurities removed by adsorption by a zeolite include substances containing water, substances containing hydrogen fluoride, substances containing a hydrocarbon, substances containing a halogenated carbon compound, substances containing a halogenated hydrocarbon compound (e.g., HFC-134), and isomers of a fluorine-containing compound to be brought into contact with a zeolite (e.g., a regioisomer with a carbon-carbon double bond, and a cyclic isomer).

The impurities specifically include heptafluorobutene, chloroheptafluorobutene, methyl iodide, and chlorotrifluoroethylene.

In the semiconductor industry, it is particularly important to remove moisture from a composition containing a fluorine-based hydrocarbon compound, such as HFC-134a.

(1-2) Zeolite

The method for dehydrating a composition containing a fluorine-based hydrocarbon compound according to the present disclosure includes the step of bringing the composition containing a fluorine-based hydrocarbon compound, such as HFC-134a, into contact with a specific zeolite.

Zeolites are one type of clay mineral, and are a water-containing aluminosilicate containing alkali or alkali earth metal with regular channels (tubular micropores) and cavities (voids) formed with a rigid anionic skeleton.

Zeolites generally have the following composition: $(M^I, M^{II}_{1/2})_m(Al_mSi_nO_{2(m+n)}) \cdot xH_2O$, ($n \geq m$) ($M^I$: $Li^+$, $Na^+$, $K^+$ etc., $M^{II}$: $Ca^{2+}$, $Mg^{2+}$, $Ba^{2+}$, etc.) The cations compensate for the negative charge of the aluminosilicate skeleton.

The cations in the zeolites can be of any type, and cations for use are typically $H^+$, $Li^+$, $Na^+$, $K^+$, $Ca^{2+}$, $Mg^{2+}$ or $Ba^{2+}$.

The basic unit of the structure is a tetrahedron structure of $SiO_4$ or $AlO_4$ (these structures are collectively referred to as TO4 tetrahedron), and these are infinitely connected in a three-dimensional direction to form a crystal. The crystal of zeolites is porous and its pore has a diameter of typically about 0.2 nm to about 1.0 nm (2 Å to 10 Å). Zeolites have a molecular sieve action, such that molecules larger than the pore diameter of zeolites are unable to enter the zeolites. Zeolites have properties such as solid acidity, ion exchange ability, catalytic ability, and adsorption ability, in addition to the molecular sieve effect due to the pores derived from the skeleton structure.

In the present disclosure, bringing a composition containing a fluorine-based hydrocarbon compound, such as HFC-134a, into contact with a specific zeolite means that the fluorine-based hydrocarbon compound, such as HFC-134a, is passed through a column filled with a zeolite; or that the fluorine-based hydrocarbon compound, such as HFC-134a, is packed in a container filled with a zeolite.

In the present disclosure, the usage form of the zeolite for use is not limited. A composition containing a fluorine-based hydrocarbon compound, such as HFC-134a, may be circulated in an apparatus filled with a zeolite; or a composition containing a fluorine-based hydrocarbon compound, such as HFC-134a, may be packed in a container filled with a zeolite and then the composition after dehydration containing a fluorine-based hydrocarbon compound, such as HFC-134a, may be extracted after a predetermined time has passed.

The method for dehydrating a composition containing a fluorine-based hydrocarbon compound according to the present disclosure includes the step of bringing the composition containing a fluorine-based hydrocarbon compound into contact with the zeolite having a ratio of silica to alumina ($SiO_2/Al_2O_3$) of 5 or more described below, or the step of bringing the composition containing a fluorine-based hydrocarbon compound into contact with at least one zeolite selected from the group consisting of chabazite zeolite, mordenite zeolite, beta zeolite, and zeolite Y.

Zeolite with a Ratio of Silica to Alumina ($SiO_2/Al_2O_3$ Ratio) of 5 or More

In the present disclosure, a zeolite with a molar ratio of silica to alumina ($SiO_2/Al_2O_3$ ratio) of 5 or more is used from the following standpoints: dehydration treatment can be efficiently performed on a composition containing a fluorine-based hydrocarbon compound, such as HFC-134a, and the release of moisture from the zeolite is well suppressed even after dehydration treatment time passes; more preferably, HFC-134 can be efficiently removed from the composition containing a fluorine-based hydrocarbon compound, such as HFC-134a. In the present disclosure, the $SiO_2/Al_2O_3$ ratio of the zeolite for use is preferably 5.5 or more, and more preferably 6 or more.

In the present disclosure, the $SiO_2/Al_2O_3$ ratio of the zeolite for use is preferably 50 or less, more preferably 45 or less, and still more preferably 40 or less.

In the present disclosure, a $SiO_2/Al_2O_3$ ratio of less than 5 leads to an increased polarity of the zeolite, and a $SiO_2/Al_2O_3$ ratio of more than 50 leads to a decreased polarity of the zeolite; thus, a zeolite with a $SiO_2/Al_2O_3$ ratio of 5 to 50 is preferably used.

In the present disclosure, a $SiO_2/Al_2O_3$ ratio of less than 5 leads to an increased polarity of the zeolite, and a $SiO_2/Al_2O_3$ ratio of more than 50 leads to a decreased polarity of the zeolite; thus, a zeolite with a $SiO_2/Al_2O_3$ ratio of 5 to 50 is preferably used.

(i) Chabazite Zeolite

A chabazite (CHA) structure is a three-dimensional porous structure with a pore diameter of about 0.38 nm (3.8 Å) and a large cage in its inside.

In the present disclosure, chabazite (CHA) zeolite is used from the following standpoints: dehydration treatment can be efficiently performed on a composition containing a fluorine-based hydrocarbon compound, such as HFC-134a, and the release of moisture from the zeolite is well suppressed even after dehydration treatment time passes; more preferably, HFC-134 can be efficiently removed from the composition containing a fluorine-based hydrocarbon compound, such as HFC-134a. In the present disclosure, specific chabazite zeolites among the commercially available products can be used.

The chabazite group includes gmelinite zeolite, erionite zeolite, levynite zeolite, and chabazite zeolite.

In the present disclosure, chabazite zeolite means that the chabazite zeolite belongs to the chabazite group, and the zeolite for use is preferably at least one type selected from the group consisting of chabazite zeolite, gmelinite zeolite, erionite zeolite, and levynite zeolite. In the present disclosure, the chabazite zeolite for use is more preferably chabazite zeolite, or a mixed zeolite (synthetic zeolite) containing chabazite zeolite and another zeolite of the chabazite group such as gmelinite, erionite, or levynite zeolite, and still more preferably a mixed zeolite (synthetic zeolite) containing chabazite zeolite and erionite zeolite as another zeolite of the chabazite group.

In the present disclosure, the crystalline system of chabazite zeolite is specifically a mixture of chabazite and erionite, which are natural minerals; i.e., a synthetic zeolite composed of a mixture of a synthetic zeolite of chabazite type (chabazite zeolite) and a synthetic zeolite of erionite type (erionite zeolite) is preferably used.

Whereas chabazite, which is a natural mineral, typically has a ratio of silica to alumina ($SiO_2/Al_2O_3$) of about 2, the synthetic chabazite zeolite has a ratio of silica to alumina ($SiO_2/Al_2O_3$) of about 6.1 to 6.7.

(ii) Mordenite Zeolite

Mordenite is also referred to as morden fusseki, and its chemical formula is $(Ca, K_2, Na_2) [AlSi_5O_{12}]_2 \cdot 7H_2O$. Mordenite is a silicate mineral. Mordenite zeolite typically has a mordenite porous structure containing 12-membered-ring pores and 8-membered-ring pores in which $SiO_4$ and $AlO_4$ share oxygen atoms and are bonded to each other. The diameter of the 12-membered-ring pore is about 0.67 nm×0.70 nm, and the diameter of the 8-membered-ring pore is about 0.29 nm×0.57 nm.

In the present disclosure, mordenite zeolite is used from the standpoints that dehydration treatment can be efficiently performed on a composition containing a fluorine-based hydrocarbon compound, such as HFC-134a, and the release of moisture from the zeolite is well suppressed even after dehydration treatment time passes, and more preferably that HFC-134 can be efficiently removed from the composition containing a fluorine-based hydrocarbon compound, such as HFC-134a. In the present disclosure, specific mordenite zeolites among the commercially available products can be used.

(iii) Beta Zeolite

Beta zeolite is one type of crystalline aluminosilicate containing Si and Al and has a three-dimensional porous structure containing 12-membered-ring pores.

In the present disclosure, beta zeolite is used from the standpoints that dehydration treatment can be efficiently performed on a composition containing a fluorine-based hydrocarbon compound, such as HFC-134a, and the release of moisture from the zeolite is well suppressed even after dehydration treatment time passes, and more preferably that HFC-134 can be efficiently removed from the composition containing a fluorine-based hydrocarbon compound, such as HFC-134a. In the present disclosure, specific beta zeolites among the commercially available products can be used.

(iv) Zeolite Y

Zeolite Y has pore openings with a diameter of about 0.74 nm, which is the largest among the commercially available zeolites.

In the present disclosure, zeolite Y can be used from the standpoints that dehydration treatment can be efficiently performed on a composition containing a fluorine-based hydrocarbon compound, such as HFC-134a, and the release of moisture from the zeolite is well suppressed even after dehydration treatment time passes, and more preferably that HFC-134 can be efficiently removed from the composition containing a fluorine-based hydrocarbon compound, such as HFC-134a. In the present disclosure, specific zeolite Ys among the commercially available products can be used.

Pore Size of Zeolite

In the present disclosure, preferably zeolites having a mean pore size of 3 Å to 15 Å can be used from the standpoints that dehydration treatment can be efficiently performed on a composition containing a fluorine-based hydrocarbon compound, such as HFC-134a, and the release of moisture from the zeolite is well suppressed even after dehydration treatment time passes, and more preferably that HFC-134 can be efficiently removed from the composition containing a fluorine-based hydrocarbon compound, such as HFC-134a. In the present disclosure, the mean pore size of the zeolite for use is more preferably 4 Å to 12 Å, and particularly preferably 5 Å to 10 Å.

In the present disclosure, the zeolite is preferably porous.

In the present disclosure, due to the zeolite for use having a mean pore size of 3 Å to 15 Å, when the fluorine-based hydrocarbon compound contained in the composition is preferably a compound having two carbon atoms (C2 compound) to eight carbon atoms (C8 compound), more preferably C2 compound to C4 compound, the composition has the advantages in that dehydration treatment can be efficiently performed on a composition containing a fluorine-based hydrocarbon compound, such as HFC-134a, and more preferably that HFC-134 can be efficiently removed from the composition containing a fluorine-based hydrocarbon compound, such as HFC-134a.

Cationic Species of Zeolite

In the present disclosure, the cationic species (cation member) of the zeolite for use is preferably $H^+$, $Li^+$, $Na^+$, $K^+$, $Ca^{2+}$, $Mg^{2+}$, $Ba^{2+}$ or the like, and more preferably $H^+$, $Na^+$ or the like from the standpoint that dehydration treatment can be efficiently performed on a composition containing a fluorine-based hydrocarbon compound, such as HFC-134a, and the release of moisture from the zeolite is well suppressed even after dehydration treatment time passes, and more preferably that HFC-134 can be efficiently removed from the composition containing a fluorine-based hydrocarbon compound, such as HFC-134a.

In the present disclosure, the cations in the zeolite undergo electrostatic interaction with water, thereby allowing dehydration treatment to efficiently proceed.

Specific Surface Area of Zeolite

In the present disclosure, the specific surface area of the zeolite measured according to BET theory ("BET specific surface area" below) is preferably 50 m²/g to 3,000 m²/g, more preferably 100 m²/g to 1,000 m²/g, still more preferably 200 m²/g to 800 m²/g, and particularly preferably 250 m²/g to 700 m²/g from the standpoint that dehydration treatment can be efficiently performed on a composition containing a fluorine-based hydrocarbon compound, such as HFC-134a, and the release of moisture from the zeolite is well suppressed even after dehydration treatment time passes, and more preferably that HFC-134 can be efficiently removed from the composition containing a fluorine-based hydrocarbon compound, such as HFC-134a.

In the present disclosure, due to the BET specific surface area of the catalyst zeolite falling within the numerical ranges above, the zeolite particles do not have an overly low density; thus, there are advantages in that dehydration treatment can be efficiently performed, and more preferably that HFC-134 can be efficiently removed from the composition containing a fluorine-based hydrocarbon compound, such as HFC-134a.

Form of Zeolite

The zeolite for use in the present disclosure is preferably porous.

In the present disclosure, the zeolite for use may be in the form of powder, granules, or pellets, or in the form of a molded article. The zeolite for use is preferably in the form of a molded article from an industrial viewpoint. Although the molded article can be of any shape, the molded article, for example, preferably has a cylindrical shape with a diameter of about 0.5 mm to 5 mm and a length of about 1 mm to about 15 mm, or a spherical shape with a diameter of about 0.5 mm to about 10 mm.

In the present disclosure, the method for producing a molded article of a zeolite can be any method, and may be, for example, a known method using kaolin clay as a binder.

The zeolite for use in the present disclosure is commercially available.

Preferable Zeolite

In the present disclosure, as described above, preferably at least one zeolite having a ratio of silica to alumina ($SiO_2$/$Al_2O_3$ ratio) (molar ratio) of 5 or more selected from the group consisting of chabazite zeolite, mordenite zeolite, beta zeolite, and zeolite Y is used from the standpoint that dehydration treatment can be efficiently performed on a composition containing a fluorine-based hydrocarbon compound, such as HFC-134a, and the release of moisture from the zeolite is well suppressed even after dehydration treatment time passes, and more preferably that HFC-134 can be efficiently removed from the composition containing a fluorine-based hydrocarbon compound, such as HFC-134a.

(1-3) Step of Bringing a Composition Containing a Fluorine-Based Hydrocarbon Compound into Contact with a Zeolite The method for dehydrating a composition containing a fluorine-based hydrocarbon compound according to the present disclosure includes the step of bringing a composition containing a fluorine-based hydrocarbon compound into contact with a zeolite having a ratio of silica to alumina ($SiO_2$/$Al_2O_3$) of 5 or more, and/or the step of bringing the composition into contact with at least one zeolite selected from the group consisting of chabazite zeolite, mordenite zeolite, beta zeolite, and zeolite Y. The dehydration method further preferably includes the step of bringing the composition containing a fluorine-based hydrocarbon compound into contact with the zeolite to remove HFC-134.

In the present disclosure, bringing the composition into contact with the zeolite means that the composition is passed through a column or the like device filled with the zeolite, or that the composition is packed in a container filled with the zeolite.

In the present disclosure, the zeolite is used as a material for removing moisture (dehydrating agent), and the moisture contained in a composition containing a fluorine-based hydrocarbon compound is removed by bringing (passing through) the composition into contact with the zeolite. The dehydration method preferably further removes HFC-134 contained in the composition.

In the present disclosure, in order to effectively remove moisture (dehydrate), and more preferably to effectively remove HFC-134, a composition containing a fluorine-based hydrocarbon compound is brought into contact with the zeolite in a mass ratio (a composition containing a fluorine-based hydrocarbon compound:zeolite) of preferably about 100:1 to 1:10, more preferably about 50:1 to 1:5, and still more preferably about 10:1 to 1:3. In the present disclosure, in regards to the amount of the zeolite for use, for example, about 10 g to 100 g of a composition containing a fluorine-based hydrocarbon compound can be brought into contact with 10 g of a packed product of zeolite (e.g., a stainless steel cylinder).

In the present disclosure, the zeolite may be subjected to activation treatment before use. The conditions for activation treatment are preferably drying treatment such as heating overnight in a vacuum ($10^{-1}$ mmHg to $10^{-3}$ mmHg) or in an inert gas stream, such as nitrogen, at a temperature within the range of 150° C. to 300° C. at which the crystalline architecture of the zeolite is maintained.

In the present disclosure, a zeolite that is not subjected to such an activation treatment can also be suitably used.

In the present disclosure, the form of the use of the zeolite is not limited. A composition containing a fluorine-based hydrocarbon compound may be circulated in a device filled with the zeolite, or a composition containing a fluorine-based hydrocarbon compound may be packed in a container filled with the zeolite and taken out after a predetermined time.

In the present disclosure, the temperature at which a composition containing a fluorine-based hydrocarbon compound is brought into contact with the zeolite is not limited. The temperature can be determined, for example, taking into consideration the boiling point of the fluorine-based hydrocarbon compound, such as HFC-134a, contained in the composition containing a fluorine-based hydrocarbon compound. Typically, the composition is preferably brought into contact with a zeolite at a low temperature because side reactions such as isomerization of the fluorine-based hydrocarbon compound are suppressed during the contact. The temperature is preferably within the range of about −50° C. to about 100° C.

In the present disclosure, the time during which a composition containing a fluorine-based hydrocarbon compound is in contact with the zeolite is not limited.

Preferable Contact Step

In the method for dehydrating a composition containing a fluorine-based hydrocarbon compound according to the present disclosure, the contact step may be either (i) the step of bringing the composition containing a fluorine-based hydrocarbon compound, such as HFC-134a, into contact with a zeolite having a ratio of silica to alumina ($SiO_2/Al_2O_3$) of 5 or more; or (ii) the step of bringing the composition containing a fluorine-based hydrocarbon compound, such as HFC-134a, into contact with at least one zeolite selected from the group consisting of chabazite zeolite, mordenite zeolite, beta zeolite, and zeolite Y; or (iii) a combination of the step of bringing the composition containing a fluorine-based hydrocarbon compound, such as HFC-134a, into contact with a zeolite having a ratio of silica to alumina ($SiO_2/Al_2O_3$) of 5 or more, and the step of bringing the composition containing a fluorine-based hydrocarbon compound, such as HFC-134a, into contact with at least one zeolite selected from the group consisting of chabazite zeolite, mordenite zeolite, beta zeolite, and zeolite Y.

In the method for dehydrating a composition containing a fluorine-based hydrocarbon compound according to the present disclosure, the contact step may be a step of bringing the composition containing a fluorine-based hydrocarbon compound, such as HFC-134a, into contact with (iv) at least one zeolite having a ratio of silica to alumina ($SiO_2/Al_2O_3$) of 5 or more selected from the group consisting of chabazite zeolite, mordenite zeolite, beta zeolite, and zeolite Y.

(1-4) Contact Step in Gas a Phase

In the method for dehydrating a composition containing a fluorine-based hydrocarbon compound according to the present disclosure, the following steps are preferably performed in a gas phase as described above: the step of bringing a composition containing a fluorine-based hydrocarbon compound into contact with a zeolite having a ratio of silica to alumina ($SiO_2/Al_2O_3$) of 5 or more, the step of bringing a composition containing a fluorine-based hydrocarbon compound into contact with at least one zeolite selected from the group consisting of chabazite zeolite, mordenite zeolite, beta zeolite, and zeolite Y, and/or the step of bringing a composition containing a fluorine-based hydrocarbon compound into contact with at least one zeolite having a ratio of silica to alumina ($SiO_2/Al_2O_3$) of 5 or more selected from the group consisting of chabazite zeolite, mordenite zeolite, beta zeolite, and zeolite Y.

In the method for dehydrating a composition containing a fluorine-based hydrocarbon compound according to the present disclosure, the contact step is preferably performed in a gas phase, particularly in a gas-phase continuous flow process using a fixed bed reactor. Performing the contact step in a gas-phase continuous flow process can simplify the apparatus, operation, and the like, and is also economically advantageous.

Temperature in the Contact Step in a Gas Phase

In the method for dehydrating a composition containing a fluorine-based hydrocarbon compound according to the present disclosure, the temperature at which the composition containing a fluorine-based hydrocarbon compound is brought into contact with a specific zeolite in a gas phase is not limited.

In the contact step according to present disclosure, the lower limit of the temperature at which the contact is performed in a gas phase is preferably −30° C., and more preferably −20° C. from the standpoint that dehydration treatment can be efficiently performed on a composition containing a fluorine-based hydrocarbon compound, such as HFC-134a, and the release of moisture from the zeolite is well suppressed even after dehydration treatment time passes, and more preferably that HFC-134 can be efficiently removed from the composition containing a fluorine-based hydrocarbon compound, such as HFC-134a.

In the contact step according to present disclosure, the upper limit of the temperature at which the contact is performed in a gas phase is about 100° C.

In the contact step according to present disclosure, the temperature at which the contact is performed in a gas phase is preferably a low temperature due to strong adsorption power.

In the contact step according to present disclosure, the temperature at which the contact is performed in a gas phase is most preferably room temperature taking into consideration facility operation and facility handling.

Time for the Contact Step in a Gas Phase

In the method for dehydrating a composition containing a fluorine-based hydrocarbon compound according to the present disclosure, the time during which the composition containing a fluorine-based hydrocarbon compound is brought into contact with a specific zeolite in a gas phase is not limited.

In the method for dehydrating a composition containing a fluorine-based hydrocarbon compound according to the present disclosure, dehydration treatment can be efficiently performed on a composition containing a fluorine-based hydrocarbon compound, such as HFC-134a, by suitably adjusting the reaction temperature and the reaction time (contact time) during which the contact is performed in a gas phase, and there are advantages in that the release of moisture from the zeolite is well suppressed even after dehydration treatment time passes, and more preferably that HFC-134 can be efficiently removed from the composition containing a fluorine-based hydrocarbon compound, such as HFC-134a.

Pressure in the Contact Step in a Gas Phase

In the method for dehydrating a composition containing a fluorine-based hydrocarbon compound according to the present disclosure, the pressure under which the composition containing a fluorine-based hydrocarbon compound is brought into contact with a specific zeolite in a gas phase is not limited.

In the step of performing chlorination reaction according to the present disclosure, the pressure under which the contact is performed is preferably −0.05 MPa to 2 MPa, more preferably −0.01 MPa to 1 MPa, and still more preferably ordinary pressure to 0.5 MPa from the standpoint that dehydration treatment can be efficiently performed on a composition containing a fluorine-based hydrocarbon compound, such as HFC-134a, and the release of moisture from the zeolite is well suppressed even after dehydration treatment time passes, and more preferably that HFC-134 can be efficiently removed from the composition containing a fluorine-based hydrocarbon compound, such as HFC-134a.

In the present disclosure, the pressure is gauge pressure unless indicated otherwise.

Vessel in the Contact Step in a Gas Phase

In the method for dehydrating a composition containing a fluorine-based hydrocarbon compound according to the present disclosure, the shape and structure of the reactor for bringing the composition containing a fluorine-based hydrocarbon compound into contact with a specific zeolite in a gas phase is not limited as long as the reactor withstands the temperature and pressure described above. Examples of such reactors include vertical reactors, horizontal reactors, and multi-tube reactors. Examples of reactor materials include glass, stainless steel, iron, nickel, and iron-nickel alloy.

Examples of the Contact Step in a Gas Phase

The method for dehydrating a composition containing a fluorine-based hydrocarbon compound according to the present disclosure can be performed in a flow process in which the composition containing a fluorine-based hydrocarbon compound is continuously brought into contact with a specific zeolite in a gas phase in the reactor to continuously take out the fluorine-based hydrocarbon compound after dehydration treatment from the reactor, or in a batch process. The method is preferably performed in a flow process to avoid the accumulation of the fluorine-based hydrocarbon compound after dehydration treatment in the reactor.

In the method for dehydrating a composition containing a fluorine-based hydrocarbon compound according to the present disclosure, the step of bringing the composition containing a fluorine-based hydrocarbon compound into contact with a specific zeolite is preferably performed in a gas phase, particularly in a gas-phase continuous flow process in a fixed bed reactor. Performing the contact step in a gas-phase continuous flow process can simplify the apparatus, operation, and the like, and is also economically advantageous.

In the method for dehydrating a composition containing a fluorine-based hydrocarbon compound according to the present disclosure, the dehydration treatment in a gas phase may be performed in the presence of an inert gas from the standpoint of reducing the degradation of the zeolite. The inert gas is preferably at least one member selected from the group consisting of nitrogen, helium, argon, and carbon dioxide. Of these inert gasses, from the standpoint of reduced cost, nitrogen is more preferable. The concentration of the inert gas is preferably 0 to 50 mol % of the gas component introduced into the reactor.

In the method for dehydrating a composition containing a fluorine-based hydrocarbon compound according to the present disclosure, the dehydration treatment in a gas phase is preferably performed in the absence of an inert gas.

In the method for dehydrating a composition containing a fluorine-based hydrocarbon compound according to the present disclosure, after the composition containing a fluorine-based hydrocarbon compound is brought into contact with a specific zeolite in a gas phase, purification treatment may optionally be performed in accordance with an ordinary method to obtain a dehydrated fluorine-based hydrocarbon compound.

In the method for dehydrating a composition containing a fluorine-based hydrocarbon compound according to the present disclosure, dehydration treatment can be efficiently performed on a composition containing a fluorine-based hydrocarbon compound, such as HFC-134a, by bringing the composition containing a fluorine-based hydrocarbon compound into contact with a specific zeolite in a gas phase, and there are advantages in that the release of moisture from the zeolite is well suppressed even after dehydration treatment time passes, and more preferably that HFC-134 can be efficiently removed from the composition containing a fluorine-based hydrocarbon compound, such as HFC-134a.

(1-5) Contact Step in a Liquid Phase

In the method for dehydrating a composition containing a fluorine-based hydrocarbon compound according to the present disclosure, as described above, the step of bringing a composition containing a fluorine-based hydrocarbon compound into contact with a zeolite having a ratio of silica to alumina ($SiO_2/Al_2O_3$) of 5 or more, the step of bringing a composition containing a fluorine-based hydrocarbon compound into contact with chabazite zeolite, and/or the step of bringing a composition containing a fluorine-based hydrocarbon compound into contact with chabazite zeolite having a ratio of silica to alumina ($SiO_2/Al_2O_3$) of 5 or more is preferably performed in a liquid phase.

Solvent for the Contact Step in a Liquid Phase

In the method for dehydrating a composition containing a fluorine-based hydrocarbon compound according to the present disclosure, the contact step performed in a liquid phase does not require a solvent if the fluorine-based hydrocarbon compound is in its liquid form.

Temperature for the Contact Step in a Liquid Phase

In the method for dehydrating a composition containing a fluorine-based hydrocarbon compound according to the present disclosure, the temperature at which the composition containing a fluorine-based hydrocarbon compound is brought into contact with a specific zeolite in a liquid phase is not limited.

In the contact step according to the present disclosure, the lower limit of the temperature at which the contact is performed in a liquid phase is preferably −30° C., and more preferably −20° C. from the standpoint that dehydration treatment can be efficiently performed on a composition containing a fluorine-based hydrocarbon compound, such as HFC-134a, and the release of moisture from the zeolite is well suppressed even after dehydration treatment time passes, and more preferably that HFC-134 can be efficiently removed from the composition containing a fluorine-based hydrocarbon compound, such as HFC-134a.

In the contact step according to the present disclosure, the upper limit of the temperature at which the contact is performed in a liquid phase is about 100° C.

In the contact step according to the present disclosure, the temperature at which the contact is performed in a liquid phase is preferably a low temperature due to strong adsorption power. In the contact step according to the present disclosure, the temperature at which the contact is performed in a liquid phase is most preferably room temperature taking into consideration facility operation and facility handling.

Pressure in the Contact Step in a Liquid Phase

In the method for dehydrating a composition containing a fluorine-based hydrocarbon compound according to the present disclosure, the reactor can be any reactor as long as the composition containing a fluorine-based hydrocarbon compound can be brought into contact with a specific zeolite in a liquid phase. The conditions for the liquid phase can be any conditions as long as the composition containing a fluorine-based hydrocarbon compound can be liquefied well, and may be a reaction of the fluorine-based hydrocarbon compound under saturated vapor pressure.

Sealed Reaction System and/or Pressure-Increased Reaction System in a Liquid Phase In the method for dehydrating a composition containing a fluorine-based hydrocarbon compound according to the present disclosure, the pressure in the reactor is not limited as long as the composition containing a fluorine-based hydrocarbon compound can be brought into contact with a specific zeolite in a liquid phase.

In the method for dehydrating a composition containing a fluorine-based hydrocarbon compound according to the present disclosure, the step of bringing the composition containing a fluorine-based hydrocarbon compound into contact with a specific zeolite in a liquid phase is preferably performed in a sealed reaction system and/or a pressure-increased reaction system from the standpoint that dehydration treatment can be efficiently performed on a composition containing a fluorine-based hydrocarbon compound, such as HFC-134a, and the release of moisture from the zeolite is well suppressed even after dehydration treatment time passes, and more preferably that HFC-134 can be efficiently removed from the composition containing a fluorine-based hydrocarbon compound, such as HFC-134a.

In the method for dehydrating a composition containing a fluorine-based hydrocarbon compound according to the present disclosure, the shape and structure of the reactor for bringing the composition containing a fluorine-based hydrocarbon compound into contact with a specific zeolite in a liquid phase is not limited as long as the reactor withstands the reaction.

In the method for dehydrating a composition containing a fluorine-based hydrocarbon compound according to the present disclosure, it is preferable to perform a reaction by using a batch-mode pressure-resistant reactor with a reaction system sealed (as a sealed reaction system in a liquid phase).

In the method for dehydrating a composition containing a fluorine-based hydrocarbon compound according to the present disclosure, the reaction pressure for a pressure-increased reaction system in a liquid phase is preferably set to a saturated vapor pressure or higher of the target fluorine-based hydrocarbon compound as the conditions for liquefaction.

In the present disclosure, the reaction pressure is gauge pressure unless indicated otherwise.

In the method for dehydrating a composition containing a fluorine-based hydrocarbon compound according to the present disclosure, the reactor for a sealed reaction system and/or a pressure-increased reaction system in a liquid phase can be any reactor. For example, it is preferred that the composition containing a fluorine-based hydrocarbon compound and other components be placed in a pressure vessel such as an autoclave and heated to an appropriate reaction temperature with a heater to allow a reaction to proceed with stirring for a predetermined time. Examples of reactor materials include glass, stainless steel, iron, nickel, and iron-nickel alloy. The reaction is preferably performed in an inert gas atmosphere such as nitrogen, helium, or carbon dioxide. For example, the reaction is preferably performed in a batch-mode pressure-resistant reactor (e.g., an autoclave) with the reaction system sealed. Examples of reactor materials include glass, stainless steel, iron, nickel, and iron-nickel alloy.

In the method for dehydrating a composition containing a fluorine-based hydrocarbon compound according to the present disclosure, the reaction pressure for a pressure-increased reaction system in a liquid phase is a pressure inside the reactor for use for the pressure-increased reaction system. In the method for dehydrating a composition containing a fluorine-based hydrocarbon compound according to the present disclosure, the reaction pressure under which the composition containing a fluorine-based hydrocarbon compound is brought into contact with a specific zeolite is preferably a condition that allows for liquefaction, more preferably 0.5 MPa or more, still more preferably 0.7 MPa or more, and particularly preferably 1.0 MPa or more from the standpoint that dehydration treatment can be efficiently performed on the composition containing a fluorine-based hydrocarbon compound, such as HFC-134a, and the release of moisture from the zeolite is well suppressed even after dehydration treatment time passes.

In the method for dehydrating a composition containing a fluorine-based hydrocarbon compound according to the present disclosure, the upper limit of the reaction pressure under which the composition containing a fluorine-based hydrocarbon compound is brought into contact with a specific zeolite in a liquid phase is about 1.0 MPa from the same viewpoints as described above. In regards to the application of pressure, the pressure inside the reaction system can be increased by introducing an inert gas, such as nitrogen, helium, or carbon dioxide, into the reaction system.

In the method for dehydrating a composition containing a fluorine-based hydrocarbon compound according to the present disclosure, the step of bringing the composition containing a fluorine-based hydrocarbon compound into contact with a specific zeolite in a liquid phase may be performed in a continuous reaction mode under an increased pressure while extracting the liquid or gasifying the product, for example, by using a method in which a back-pressure valve is connected to a continuous stirred-tank reactor (CSTR).

In the method for dehydrating a composition containing a fluorine-based hydrocarbon compound according to the present disclosure, after the composition containing a fluorine-based hydrocarbon compound is brought into contact with a specific zeolite in a liquid phase, purification treatment may optionally be performed in accordance with an ordinary method to obtain a dehydrated fluorine-based hydrocarbon compound.

In the method for dehydrating a composition containing a fluorine-based hydrocarbon compound according to the present disclosure, dehydration treatment can be efficiently performed on a composition containing a fluorine-based hydrocarbon compound, such as HFC-134a by bringing the composition containing a fluorine-based hydrocarbon compound into contact with a specific zeolite in a liquid phase in a sealed reaction system and/or a pressure-increased reaction system, and there are advantages in that the release of moisture from the zeolite is well suppressed even after dehydration treatment time passes, and more preferably that HFC-134 can be efficiently removed from the composition containing a fluorine-based hydrocarbon compound, such as HFC-134a.

(1-6) Making the Moisture Content or/and the HFC-134 Content Less than 3 ppmwt

The method for dehydrating a composition containing a fluorine-based hydrocarbon compound according to the present disclosure reduces the release of moisture adsorbed by a zeolite even after time passes because of the use of a zeolite having a ratio of silica to alumina ($SiO_2/Al_2O_3$) of 5 or more or at least one zeolite selected from the group consisting of chabazite zeolite, mordenite zeolite, beta zeolite, and zeolite Y when dehydrating a composition containing a fluorine-based hydrocarbon compound, such as HFC-134a.

The method for dehydrating a composition containing a fluorine-based hydrocarbon compound according to the present disclosure enables the composition after dehydration, i.e., the composition after coming into contact with the zeolite (the composition containing a fluorine-based hydrocarbon compound, such as HFC-134a) to have a moisture content of less than about 10 ppmwt (mass/mass), and preferably less than about 3 ppmwt. In the present disclosure, the minimum value of the moisture content in the composition after dehydration is about 0.1 ppmwt.

The method for dehydrating a composition containing a fluorine-based hydrocarbon compound according to the present disclosure enables the composition after dehydration, i.e., the composition after coming into contact with a zeolite (a composition containing a fluorine-based hydrocarbon compound, such as HFC-134a) to have an HFC-134 content of less than about 10 ppmwt (mass/mass), and preferably less than about 3 ppmwt. In the present disclosure, the minimum value of the HFC-134 content in the composition after dehydration is about 0.1 ppmwt.

The method for dehydrating a composition containing a fluorine-based hydrocarbon compound according to the present disclosure enables the composition containing a fluorine-based hydrocarbon compound, such as HFC-134a, to more preferably have a moisture content of less than about 3 ppmwt, and an HFC-134 content of less than about 3 ppmwt.

In the present disclosure, because of effective dehydration (removal) of the moisture in a composition containing a fluorine-based hydrocarbon compound, such as HFC-134a, the fluorine-based hydrocarbon compound, such as HFC-134a, from which moisture is dehydrated (removed), more preferably the fluorine-based hydrocarbon compound, such as HFC-134a, from which HFC-134 is removed, can be suitably used as etching gas in semiconductor production. Corrosion or early deterioration of equipment can also be suppressed.

(2) The Method for Producing a Composition Containing a Fluorine-Based Hydrocarbon Compound The method for producing a composition containing a fluorine-based hydrocarbon compound according to the present disclosure includes the step of bringing the composition containing a fluorine-based hydrocarbon compound into contact with a zeolite having a ratio of silica to alumina ($SiO_2/Al_2O_3$) of 5 or more, wherein the fluorine-based hydrocarbon compound contains at least one compound selected from the group consisting of HFC-134a, HFC-125, HFC-32, and HFO-1234yf.

The method for producing a composition containing a fluorine-based hydrocarbon compound according to the present disclosure includes the step of bringing the composition containing a fluorine-based hydrocarbon compound into contact with at least one zeolite selected from the group consisting of chabazite zeolite, mordenite zeolite, beta zeolite, and zeolite Y wherein the fluorine-based hydrocarbon compound contains at least one compound selected from the group consisting of HFC-134a, HFC-125, HFC-32, and HFO-1234yf.

The method for producing a composition containing a fluorine-based hydrocarbon compound according to the present disclosure preferably further includes the step of bringing the composition containing a fluorine-based hydrocarbon compound into contact with the zeolite to remove HFC-134.

The step of bringing the composition containing a fluorine-based hydrocarbon compound into contact with various types of zeolites can be the step of the dehydration method described above.

In the method for producing a composition containing a fluorine-based hydrocarbon compound according to the present disclosure, the composition after coming into contact with the zeolite has a moisture content of less than about 10 ppmwt, and preferably less than about 3 ppmwt. In the present disclosure, the minimum value of the moisture content in the composition is about 0.1 ppmwt.

In the method for producing a composition containing a fluorine-based hydrocarbon compound according to the present disclosure, the composition after coming into contact with the zeolite has an HFC-134 content of less than about 10 ppmwt, and preferably less than about 3 ppmwt. In the present disclosure, the minimum value of the HFC-134 content in the composition is about 0.1 ppmwt.

In the method for producing a composition containing a fluorine-based hydrocarbon compound according to the present disclosure, the composition after coming into contact with the zeolite more preferably has a moisture content of less than about 3 ppmwt, and an HFC-134 content of less than about 3 ppmwt.

The production method according to the present disclosure is a method for producing a high-purity fluorine-based hydrocarbon compound including the step of bringing at least one fluorine-based hydrocarbon compound selected from the group consisting of 1,1,1,2-tetrafluoroethane (HFC-134a), 1,1,1,2,2-pentafluoroethane (HFC-125), difluoromethane (HFC-32), and 2,3,3,3-tetrafluoropropene (HFO-1234yf) into contact with a zeolite having a ratio of silica to alumina ($SiO_2/Al_2O_3$) of 5 or more to remove the impurity contained in the fluorine-based hydrocarbon compound.

The production method according to the present disclosure is a method for producing a high-purity fluorine-based hydrocarbon compound including the step of bringing at least one fluorine-based hydrocarbon compound selected from the group consisting of 1,1,1,2-tetrafluoroethane (HFC-134a), 1,1,1,2,2-pentafluoroethane (HFC-125), difluoromethane (HFC-32), and 2,3,3,3-tetrafluoropropene (HFO-1234yf) into contact with at least one zeolite selected from the group consisting of chabazite zeolite, mordenite zeolite, beta zeolite, and zeolite Y to remove the impurity contained in the fluorine-based hydrocarbon compound. The impurity is preferably at least one component selected from the group consisting of water and HFC-134.

The step of bringing the composition containing a fluorine-based hydrocarbon compound into contact with various types of zeolites can be the step of the dehydration method described above.

In the production method according to the present disclosure, the removed impurity is, for example, water as described above. In regards to the water concentration of the fluorine-based hydrocarbon compound after the impurity is removed, the moisture content is less than about 10 ppmwt, and preferably less than about 3 ppmwt. In the present disclosure, the minimum value of the moisture content is about 0.1 ppmwt.

In the production method according to the present disclosure, the removed impurity is, for example, HFC-134 as described above. In regards to the HFC-134 concentration of the fluorine-based hydrocarbon compound after the impurity is removed, the HFC-134 content is less than about 10 ppmwt, and preferably less than about 3 ppmwt. In the present disclosure, the minimum value of the HFC-134 content is about 0.1 ppmwt.

In regards to the water concentration and the HFC-134 concentration of the fluorine-based hydrocarbon compound after the impurity is removed, more preferably, the moisture content is less than about 3 ppmwt, and the HFC-134 content is less than about 3 ppmwt.

In the present disclosure, the step preferably allows the zeolite to adsorb the moisture in the composition containing a fluorine-based hydrocarbon compound (i.e., a composition that has yet to be brought into contact with the zeolite) to dehydrate the composition, and remove the moisture from the composition. In the present disclosure, the step more preferably removes HFC-134 from the composition containing a fluorine-based hydrocarbon compound.

In the method for producing a composition containing a fluorine-based hydrocarbon compound according to the present disclosure, the contact step may be either the step of bringing the composition containing a fluorine-based hydrocarbon compound, such as HFC-134a, into contact with a zeolite having a ratio of silica to alumina ($SiO_2/Al_2O_3$) of 5 or more or the step of bringing the composition into contact with at least one zeolite selected from the group consisting of chabazite zeolite, mordenite zeolite, beta zeolite, and zeolite Y, or a combination of the step of bringing the composition into contact with a zeolite having a ratio of silica to alumina ($SiO_2/Al_2O_3$) of 5 or more and the step of bringing the composition into contact with at least one zeolite selected from the group consisting of chabazite zeolite, mordenite zeolite, beta zeolite, and zeolite Y.

In the method for producing a composition containing a fluorine-based hydrocarbon compound according to the present disclosure, the contact step can be a step of bringing the composition containing a fluorine-based hydrocarbon compound, such as HFC-134a, into contact with at least one zeolite that has a ratio of silica to alumina ($SiO_2/Al_2O_3$) of 5 or more and that is selected from the group consisting of chabazite zeolite, mordenite zeolite, beta zeolite, and zeolite Y.

The present disclosure enables the composition after coming into contact with the zeolite, in particular the composition containing a fluorine-based hydrocarbon compound, such as HFC-134a, to have a moisture content of preferably less than 3 ppmwt.

The present disclosure enables the composition after coming into contact with the zeolite, in particular the composition containing a fluorine-based hydrocarbon compound, such as HFC-134a, to have an HFC-134 content of preferably less than 3 ppmwt.

In the method for producing a composition containing a fluorine-based hydrocarbon compound according to the present disclosure, the composition containing a fluorine-based hydrocarbon compound to be subjected to dehydration treatment, the zeolite for use, the step of bringing the composition containing a fluorine-based hydrocarbon compound into contact with a zeolite, the contact step in a gas phase, the contact step in a liquid phase, making the moisture content less than 3 ppmwt, making the HFC-134 content less than 3 ppmwt, and the like are as described for the method for dehydrating a composition containing a fluorine-based hydrocarbon compound according to the present disclosure.

(3) The Composition Containing a Fluorine-Based Hydrocarbon Compound

In the composition containing a fluorine-based hydrocarbon compound according to present disclosure, the fluorine-based hydrocarbon compound contains at least one compound selected from the group consisting of HFC-134a, HFC-125, HFC-32, and HFO-1234yf, and the moisture content is less than 3 ppmwt.

In the composition containing a fluorine-based hydrocarbon compound according to present disclosure, the fluorine-based hydrocarbon compound contains at least one compound selected from the group consisting of HFC-134a, HFC-125, HFC-32, and HFO-1234yf, and the HFC-134 content is less than 3 ppmwt.

In the composition containing a fluorine-based hydrocarbon compound according to present disclosure, more preferably, the moisture content is less than 3 ppmwt, and the HFC-134 content is less than 3 ppmwt.

Measurement of the Moisture Content

The moisture content in the composition containing a fluorine-based hydrocarbon compound according to the present disclosure is a moisture content as measured with a Karl Fischer moisture meter, and is a moisture content based on the Karl Fischer method. Specifically, the moisture content is a value determined by adding 1 g of a composition containing a fluorine-based hydrocarbon compound (liquefied gas) to a Karl Fischer moisture meter to collect the moisture in a solvent, and measuring the moisture by titration.

The moisture content (ppm) is a mass fraction obtained by dividing the moisture content (mass) of a composition containing a fluorine-based hydrocarbon compound by the mass of the composition containing a fluorine-based hydrocarbon compound (i.e., ppmwt (mass/mass)).

Measurement of the HFC-134 Content

The HFC-134 content in the composition containing a fluorine-based hydrocarbon compound according to the present disclosure can be measured based on mass spectrometry and structural analysis.

The HFC-134 content in the composition containing a fluorine-based hydrocarbon compound according to the present disclosure can be measured, for example, by performing mass spectrometry based on gas chromatography/mass spectrometry (GC/MS) by using gas chromatography (e.g., trade name: GC-2014, produced by Shimadzu Corporation) and also performing structural analysis based on an NMR spectrum by NMR (e.g., trade name: 400 YH, produced by JEOL).

In the present disclosure, the content (ppm) of the HFC-134 content when used in these instruments is a volume fraction obtained by dividing the HFC-134 content (volume) in the composition containing a fluorine-based hydrocarbon compound by the volume of the composition containing a fluorine-based hydrocarbon compound (i.e., ppmvol (volume/volume)).

The HFC-134 content (ppm) can also be paraphrased as, for example, less than 3 ppmvol.

The composition containing a fluorine-based hydrocarbon compound according to the present disclosure is preferably used in etching gas for forming state-of-the-art microstructures, such as semiconductors and liquid crystals, as well as refrigerants, and heat-transfer mediums, in the same manner as HFC-134a, HFC-125, HFC-32, HFO-1234yf, and the like. The composition containing a fluorine-based hydrocarbon compound according to the present disclosure is also effectively used in various areas, such as deposit gas, building blocks for organic synthesis, and cleaning gas, as well as etching gas.

The composition containing a fluorine-based hydrocarbon compound according to the present disclosure is preferably used in etching gas, a refrigerant, a heat-transfer medium, deposit gas, a building block for organic synthesis, or cleaning gas.

Deposit gas is for depositing an etching-resistant polymer layer.

Building blocks for organic synthesis refer to a substance that can serve as a precursor of a compound having a highly reactive skeleton. For example, a reaction of the composition containing a fluorine-based hydrocarbon compound according to the present disclosure with a fluorine-containing organic silicon compound, such as $CF_3Si(CH_3)_3$, to introduce a fluoroalkyl group such as a $CF_3$ group converts the compound into a substance that can serve as a cleaner or a fluorine-containing pharmaceutical intermediate.

The present disclosure includes the following subject matter.

Item 1.

A method for dehydrating a composition containing a fluorine-based hydrocarbon compound,
wherein the fluorine-based hydrocarbon compound is at least one compound selected from the group consisting of 1,1,1,2-tetrafluoroethane (HFC-134a), 1,1,1,2,2-pentafluoroethane (HFC-125), difluoromethane (HFC-32), and 2,3,3,3-tetrafluoropropene (HFO-1234yf),
the method comprising the step of bringing the composition containing the fluorine-based hydrocarbon compound into contact with a zeolite having a ratio of silica to alumina ($SiO_2/Al_2O_3$) of 5 or more.

Item 2.

A method for dehydrating a composition containing a fluorine-based hydrocarbon compound, wherein the fluorine-based hydrocarbon compound is at least one compound selected from the group consisting of 1,1,1,2-tetrafluoroethane (HFC-134a), 1,1,1,2,2-pentafluoroethane (HFC-125), difluoromethane (HFC-32), and 2,3,3,3-tetrafluoropropene (HFO-1234yf), the method comprising the step of bringing the composition containing the fluorine-based hydrocarbon compound into contact with at least one zeolite selected from the group consisting of chabazite zeolite, mordenite zeolite, beta zeolite, and zeolite Y.

Item 3.

The dehydration method according to Item 1 or 2, wherein the composition after dehydration in the step has a moisture content of less than 3 ppmwt (ppm by weight).

Item 4.

The dehydration method according to any one of Items 1 to 3, further comprising the step of bringing the composition containing the fluorine-based hydrocarbon compound into contact with the zeolite to remove 1,1,2,2-tetrafluoroethane (HFC-134).

The composition after dehydration in the step of the dehydration method preferably has an HFC-134 content of less than 3 ppmwt.

When the HFC-134 content (ppm) is measured, for example, by performing mass spectrometry based on gas chromatography/mass spectrometry (GC/MS) by using gas chromatography and also performing structural analysis based on an NMR spectrum by NMR, the HFC-134 content is a volume fraction obtained by dividing the HFC-134 content (volume) in the composition containing the fluorine-based hydrocarbon compound by the volume of the composition containing the fluorine-based hydrocarbon compound (i.e., ppmvol (volume/volume)).

The HFC-134 content (ppm) can also be paraphrased as, for example, less than 3 ppmvol.

Item 5.

A method for producing a composition containing a fluorine-based hydrocarbon compound, wherein the fluorine-based hydrocarbon compound is at least one compound selected from the group consisting of 1,1,1,2-tetrafluoroethane (HFC-134a), 1,1,1,2,2-pentafluoroethane (HFC-125), difluoromethane (HFC-32), and 2,3,3,3-tetrafluoropropene (HFO-1234yf), the method comprising the step of bringing a composition containing the fluorine-based hydrocarbon compound into contact with a zeolite having a ratio of silica to alumina ($SiO_2/Al_2O_3$) of 5 or more.

Item 6.

A method for producing a composition containing a fluorine-based hydrocarbon compound, wherein the fluorine-based hydrocarbon compound is at least one compound selected from the group consisting of 1,1,1,2-tetrafluoroethane (HFC-134a), 1,1,1,2,2-pentafluoroethane (HFC-125), difluoromethane (HFC-32), and 2,3,3,3-tetrafluoropropene (HFO-1234yf), the method comprising the step of bringing a composition containing the fluorine-based hydrocarbon compound into contact with at least one zeolite selected from the group consisting of chabazite zeolite, mordenite zeolite, beta zeolite, and zeolite Y.

Item 7.

The production method according to Item 5 or 6, wherein the composition after coming in contact with the zeolite has a moisture content of less than 3 ppmwt.

Item 8.

The production method according to any one of Items 5 to 7, further comprising the step of bringing the composition containing the fluorine-based hydrocarbon compound into contact with the zeolite to remove 1,1,2,2-tetrafluoroethane (HFC-134).

In the production method, the composition after coming in contact with the zeolite preferably has an HFC-134 content of less than 3 ppmwt.

Item 9.

A method for producing a high-purity fluorine-based hydrocarbon compound, the method comprising the step of bringing a composition containing at least one fluorine-based hydrocarbon compound selected from the group consisting of 1,1,1,2-tetrafluoroethane (HFC-134a), 1,1,1,2,2-pentafluoroethane (HFC-125), difluoromethane (HFC-32), and 2,3,3,3-tetrafluoropropene (HFO-1234yf) into contact with a zeolite having a ratio of silica to alumina ($SiO_2/Al_2O_3$) of 5 or more to remove an impurity contained in the fluorine-based hydrocarbon compound.

Item 10.

A method for producing a high-purity fluorine-based hydrocarbon compound, the method comprising the step of bringing a composition containing at least one fluorine-based hydrocarbon compound selected from the group consisting of 1,1,1,2-tetrafluoroethane (HFC-134a), 1,1,1,2,2-pentafluoroethane (HFC-125), difluoromethane (HFC-32), and 2,3,3,3-tetrafluoropropene (HFO-1234yf) into contact with at least one zeolite selected from the group consisting of chabazite zeolite, mordenite zeolite, beta zeolite, and zeolite Y to remove an impurity contained in the fluorine-based hydrocarbon compound.

Item 11.

The production method according to Item 9 or 10, wherein the impurity is at least one component selected from the group consisting of water and 1,1,2,2-tetrafluoroethane (HFC-134).

Item 12.

The production method according to any one of Items 9 to 11, wherein the water concentration of the fluorine-based hydrocarbon compound after impurity removal is a moisture content of less than 3 ppmwt.

In the production method, the HFC-134 concentration of the fluorine-based hydrocarbon compound after impurity removal is preferably an HFC-134 content of less than 3 ppmwt.

Item 13.

A composition containing a fluorine-based hydrocarbon compound, wherein the fluorine-based hydrocarbon compound contains at least one compound selected from the group consisting of 1,1,1,2-tetrafluoroethane (HFC-134a), 1,1,1,2,2-pentafluoroethane (HFC-125), difluoromethane (HFC-32), and 2,3,3,3-tetrafluoropropene (HFO-1234yf), and wherein the moisture content is less than 3 ppmwt or/and the HFC-134 content is less than 3 ppmwt.

Item 14.

The composition according to Item 13, which is for use in etching gas, refrigerants, heat-transfer mediums, deposit gas, building blocks for organic synthesis, or cleaning gas.

Although embodiments of the present disclosure are described above, various changes can be made in forms and details without departing from the spirit and principal concept of the scope of the claims.

EXAMPLES

The following describes the present disclosure in more detail with reference Examples. However, the present disclosure is not limited to these Examples.

Measurement of the Moisture Content in a Composition Containing a Fluorine-Based Hydrocarbon Compound The moisture content was measured with the measurement device by the method under the conditions as indicated below.

Measurement device: Kari Fischer moisture meter
Measurement condition: Coulometric titration The moisture content of the composition containing a fluorine-based hydrocarbon compound is a moisture content as measured with a Karl Fischer moisture meter, and is a moisture content based on Karl Fischer coulometric titration. Specifically, 1 g of a composition containing a fluorine-based hydrocarbon compound was added to a Karl Fischer moisture meter to collect moisture in a solvent, and the value determined by titration was used.

The moisture content (ppm) was a mass fraction obtained by dividing the moisture content (mass) in a composition containing a fluorine-based hydrocarbon compound by the mass of the composition containing a fluorine-based hydrocarbon compound (i.e., ppmwt (mass/mass)).

(1) Method for Dehydrating a Composition Containing a Fluorine-Based Hydrocarbon Compound in Examples (Liquid Phase)

Fluorine-based Hydrocarbon Compound: HFC-134a

A composition containing HFC-134a was brought into contact with chabazite zeolite (Example 1), mordenite zeolite (Example 2), beta zeolite (Example 3), or zeolite Y (Example 4), all of which had a ratio of silica to alumina ($SiO_2/Al_2O_3$) of 5 or more.

One g of individual zeolites (dehydrating agent) shown in Table 1 was added to a 75-mL stainless-steel cylinder. The cylinder was filled with a composition containing HFC-134a in a predetermined amount (10 g). The mixture was stirred, and the moisture content in the liquid phase was measured by the Karl Fischer method at the start of dehydration (0 hr), after 24 hours (24 hr), after 48 hours (48 hr), after 72 hours (72 hr), and after 96 hours (96 hr).

TABLE 1

| Zeolite in Examples (Dehydrating Agent) | Pore Diameter | Ratio of Silica to Almina ($SiO_2/Al_2O_3$) | Crystalline System | Time Passed | 0 hr | 24 hr | 48 hr | 72 hr | 96 hr |
|---|---|---|---|---|---|---|---|---|---|
| 1 | 5 Å | 6.1 | Chabazite Zeolite | Moisture Content | 6.2 ppm | 1.3 ppm | 1.03 ppm | 0.9 ppm | 0.74 ppm |
| 2 | 5 Å | 9.2 | Mordenite Zeolite | Moisture Content | 10.1 ppm | 8.9 ppm | 3.99 ppm | 2.77 ppm | 2.35 ppm |
| 3 | 6.5 Å | 40 | Beta Zeolite | Moisture Content | 6.2 ppm | 2.31 ppm | 2.07 ppm | 1.22 ppm | 1.1 ppm |
| 4 | 9 Å | 6 | Zeolite Y | Moisture Content | 6.2 ppm | 3.34 ppm | 1.43 ppm | 0.32 ppm | 0.27 ppm |

The compositions after coming into contact with the zeolites in the Examples had a moisture content of less than 3 ppmwt. When chabazite zeolite having a ratio of silica to alumina ($SiO_2/Al_2O_3$) of 5 or more was used as a dehydrating agent, moisture was not desorbed from the zeolites even after time passed, and an increase in the moisture content in the compositions containing HFC-134a was not observed.

(2) Method for Dehydrating a Composition Containing a Fluorine-Based Hydrocarbon Compound in Comparative Examples (Liquid Phase)

A composition containing HFC-134a was brought into contact with zeolite A (not chabazite zeolite) with a ratio of silica to alumina ($SiO_2/Al_2O_3$) of less than 5.

One g of individual zeolites (dehydrating agent) shown in Table 2 was added to a 75-mL stainless-steel cylinder. The cylinder was filled with a composition containing HFC-134a in a predetermined amount (10 g). The mixture was stirred, and the moisture content in a liquid phase was measured at the start of dehydration (0 hr), after 24 hours (24 hr), after 48 hours (48 hr), after 72 hours (72 hr), and after 96 hours (96 hr) by the Karl Fischer method.

TABLE 2

| Zeolite in Comparative Examples (Dehydrating Agent) | Pore Diameter | Ratio of Silica to Almina ($SiO_2/Al_2O_3$) | Crystalline System | Time Passed | 0 hr | 24 hr | 48 hr | 72 hr | 96 hr |
|---|---|---|---|---|---|---|---|---|---|
| 5 | 3 Å | 2.01 | A | Moisture Content | 6.2 ppm | 2.66 ppm | 4.45 ppm | 8.99 ppm | — |
| 6 | 4 Å | 2.11 | A | Moisture Content | 6.2 ppm | 2.56 ppm | 1.65 ppm | 1.93 ppm | 4.4 ppm |

TABLE 2-continued

| Zeolite in Comparative Examples (Dehydrating Agent) | Pore Diameter | Ratio of Silica to Almina (SiO$_2$/Al$_2$O$_3$) | Crystalline System | Time Passed | 0 hr | 24 hr | 48 hr | 72 hr | 96 hr |
|---|---|---|---|---|---|---|---|---|---|
| 7 | 5 Å | 2.33 | A | Moisture Content | 6.2 ppm | 5.46 ppm | 5.87 ppm | 3.96 ppm | 16.38 ppm |

The compositions brought into contact with the zeolites in the Comparative Examples had a moisture content of more than 3 ppmwt. When a zeolite having a ratio of silica to alumina (SiO$_2$/Al$_2$O$_3$) of about 2 was used as a dehydrating agent, the adsorbed moisture was desorbed from the zeolites after time passed, and an increase in the moisture content in the compositions containing HFC-134a was observed.

(3) Method for Dehydrating a Composition Containing a Fluorine-Based Hydrocarbon Compound in a Gas Phase Fluorine-based Hydrocarbon compound: HFC-134a HFC-134a is a sample containing 5 ppmwt (mass/mass) of water.

Activation treatment (pretreatment) was performed by heating the zeolites for use (molecular sieves (MS)) in a vacuum ($10^{-1}$ mmHg to $10^{-3}$ mmHg) at a temperature of 180° C. before use to remove water from the zeolites.

A composition containing HFC-134a (gas) was brought into contact with chabazite zeolite (Example 8) having a ratio of silica to alumina (SiO$_2$/Al$_2$O$_3$) of 5 or more, and a non-chabazite zeolite A having a ratio of silica to alumina (SiO$_2$/Al$_2$O$_3$) of less than 5 (Comparative Examples 9 and 10). In the dehydration method in a gas phase, a gas containing HFC-134a was passed through a layer of each zeolite at a W/F of 0.2 to 0.6 g/(cc/sec) at a flow rate of HFC-134a of 1.7 cm/sec.

TABLE 3

| Zeolite (Dehydrating Agent) | Effective Pore Diameter | Ratio of Silica to Almina (SiO$_2$/Al$_2$O$_3$) | Form of MS | Name of Structure Similar to Natural Minerals | Equilibrium Adsorption Amount (ug (H$_2$O)/g-MS) |
|---|---|---|---|---|---|
| Example 8 | 5 Å | 6.1 | Similar to A | Chabazite Zeolite | 51,590 |
| Comparative Example 9 | 3 Å | 2.01 | A | Synthetic zeolite not found in natural minerals | 3,380 |
| Comparative Example 10 | 4 Å | 2.11 | A | Synthetic zeolite not found in natural minerals | 38 |

The zeolite in Example 8 was able to efficiently remove water from the composition containing HFC-134a (gas) in a short time. Performing activation treatment (pretreatment) on the zeolite before use also enabled more efficient removal of water from the composition containing HFC-134a (gas) in a short time.

In contrast, the zeolites used in Comparative Examples 9 and 10 were unable to efficiently remove water from the composition containing HFC-134a (gas).

(4) Method for Removing HFC-134 from a Composition Containing a Fluorine-Based Hydrocarbon Compound in a Gas Phase Fluorine-based Hydrocarbon Compound: HFC-134a HFC-134a is a sample containing 5 ppmwt (mass/mass) of water and 500 ppmvol (volume/volume) of HFC-134.

Activation treatment (pretreatment) was performed by heating the zeolites for use (molecular sieves (MS)) in a vacuum ($10^{-1}$ mmHg to $10^{-3}$ mmHg) at a temperature of 180° C. before use to remove water from the zeolites.

A composition containing HFC-134a (gas) was brought into contact with chabazite zeolite having a ratio of silica to alumina (SiO$_2$/Al$_2$O$_3$) of 5 or more (Example 11), and non-chabazite zeolites A having a ratio of silica to alumina (SiO$_2$/Al$_2$O$_3$) of less than 5 (Comparative Examples 12 and 13). In the method for removing HFC-134 in a gas phase, a gas containing HFC-134a was passed through a layer of each zeolite at a W/F of 100 g/(cc/sec) until the HFC-134 concentration was detected at the outlet.

TABLE 4

| Zeolite (Dehydrating Agent) | Effective Pore Diameter | Ratio of Silica to Almina (SiO$_2$/Al$_2$O$_3$) | Form of MS | Name of structure similar to natural minerals | Contact Time (W/F) (g/(cc/sec)) | Breakthrough Time (min) | HFC-134 Adsorption Amount (cc(134)/g-MS)) |
|---|---|---|---|---|---|---|---|
| Example 11 | 5 Å | 6.1 | Similar to A | Chabazite Zeolite | 100 | Not having breakthrough even after 12-hr circulation | Large |

TABLE 4-continued

| Zeolite (Dehydrating Agent) | Effective Pore Diameter | Ratio of Silica to Almina (SiO$_2$/Al$_2$O$_3$) | Form of MS | Name of structure similar to natural minerals | Contact Time (W/F) (g/(cc/sec)) | Breakthrough Time (min) | HFC-134 Adsorption Amount (cc(134)/g-MS)) |
|---|---|---|---|---|---|---|---|
| Comparative Example 12 | 3 Å | 2.01 | A | Synthetic zeolite not found in natural minerals | 100 | 6 | 0.001 |
| Comparative Example 13 | 4 Å | 2.11 | A | Synthetic zeolite not found in natural minerals | 100 | 6 | 0.002 |

The zeolite in Example 11 did not exhibit a breakthrough when the composition containing HFC-134a (gas) was circulated at a W/F of 100 g/(cc/sec) for 12 hours, and HFC-134 was not detected. The zeolite in Example 11 was able to efficiently remove HFC-134 in a short time. At this time, water was not detected. Performing activation treatment (pretreatment) on the zeolite before use enabled more efficient removal of HFC-134 from the composition containing HFC-134a (gas) in a short time.

In contrast, the zeolites in Comparative Examples 12 and 13 had a breakthrough in 6 minutes, and HFC-134 was detected. The amount of detected HFC-134 continued to increase. The zeolites in Comparative Examples 12 and 13 were unable to efficiently remove HFC-134 from the composition containing HFC-134a (gas).

(5) Explanation of Chabazite (Similar to a Type) Zeolite (MS) Used in Examples

The chabazite (similar to A type) zeolite used in the Examples is a zeolite in which AlO$_4$ of zeolite 5A of zeolite A (synthetic zeolite) is replaced with SiO$_4$, and has the same crystalline architecture as that of chabazite.

As a result of X-ray diffraction, the chabazite (similar to A type) zeolite used in the Examples was found to have a crystalline system composed of a mixture of natural minerals, chabazite and erionite (i.e., a synthetic zeolite composed of a mixture of a synthetic zeolite of chabazite-type (chabazite zeolite) and a synthetic zeolite of erionite-type (erionite zeolite)).

(6) Summary of the Method for Dehydrating a Composition Containing a Fluorine-Based Hydrocarbon Compound Due to their high speed and high integration, the circuitry pattern of semiconductor integrated circuit devices is becoming finer. Fluorine-based hydrocarbon compounds, such as HFC-134a, are essential gases for etching the most minute contact holes.

The method for dehydrating a composition containing a fluorine-based hydrocarbon compound or the method for producing a composition containing a fluorine-based hydrocarbon compound according to the present disclosure has an advantage in that when a composition containing a fluorine-based hydrocarbon compound, such as HFC-134a, is dehydrated, the use of the specific zeolite described above reduces the release of moisture adsorbed by the zeolite from the zeolite even after time passes; and in that moisture is removed well from the composition containing a fluorine-based hydrocarbon compound, such as HFC-134a.

The method for dehydrating a composition containing a fluorine-based hydrocarbon compound or the method for producing a composition containing a fluorine-based hydrocarbon compound according to the present disclosure enables a composition containing a fluorine-based hydrocarbon compound, such as HFC-134a, to have a moisture content of less than 3 ppmwt. A composition containing a fluorine-based hydrocarbon compound (e.g., HFC-134a) with a moisture content of less than 3 ppmwt is advantageous in etching fine contact holes and forming fine circuitry patterns in semiconductor integrated circuit devices.

The invention claimed is:

1. A method for dehydrating a composition containing a fluorine-based hydrocarbon compound,
    wherein the fluorine-based hydrocarbon compound contains 1,1,1,2-tetrafluoroethane (HFC-134a),
    the method comprising bringing the composition into contact with a zeolite having a ratio of silica to alumina (SiO$_2$/Al$_2$O$_3$) of 5 or more to dehydrate the composition, and to remove 1,1,2,2-tetrafluoroethane (HFC-134) from the composition,
    wherein the composition after dehydration has a moisture content of less than 3 ppmwt, and has an HFC-134 content of less than 3 ppmwt.

2. A method for dehydrating a composition containing a fluorine-based hydrocarbon compound,
    wherein the fluorine-based hydrocarbon compound contains 1,1,1,2-tetrafluoroethane (HFC-134a),
    the method comprising bringing the composition into contact with at least one zeolite selected from the group consisting of chabazite zeolite, mordenite zeolite, beta zeolite, and zeolite Y to dehydrate the composition, and to remove 1,1,2,2-tetrafluoroethane (HFC-134) from the composition,
    wherein the composition after dehydration has a moisture content of less than 3 ppmwt, and has an HFC-134 content of less than 3 ppmwt.

3. A method for producing a composition containing a fluorine-based hydrocarbon compound,
    wherein the fluorine-based hydrocarbon compound contains 1,1,1,2-tetrafluoroethane (HFC-134a),
    the method comprising bringing a composition containing the fluorine-based hydrocarbon compound into contact with a zeolite having a ratio of silica to alumina (SiO$_2$/Al$_2$O$_3$) of 5 or more to produce a composition having a moisture content of less than about 3 ppmwt, and having a 1,1,2,2-tetrafluoroethane (HFC-134) content of less than 3 ppmwt.

4. A method for producing a composition containing a fluorine-based hydrocarbon compound,
wherein the fluorine-based hydrocarbon compound contains 1,1,1,2-tetrafluoroethane (HFC-134a),
the method comprising the step of bringing a composition containing the fluorine-based hydrocarbon compound into contact with at least one zeolite selected from the group consisting of chabazite zeolite, mordenite zeolite, beta zeolite, and zeolite Y to produce a composition having a moisture content of less than about 3 ppmwt, and having a 1,1,2,2-tetrafluoroethane (HFC-134) content of less than 3 ppmwt.

5. A method for producing a high-purity fluorine-based hydrocarbon compound, the method comprising the step of bringing a composition containing a fluorine-based hydrocarbon compound containing 1,1,1,2-tetrafluoroethane (HFC-134a) into contact with a zeolite having a ratio of silica to alumina ($SiO_2/Al_2O_3$) of 5 or more to remove an impurity contained in the fluorine-based hydrocarbon compound, to produce a composition having a moisture content of less than about 3 ppmwt, and having a 1,1,2,2-tetrafluoroethane (HFC-134) content of less than 3 ppmwt.

6. A method for producing a high-purity fluorine-based hydrocarbon compound, the method comprising the step of bringing a composition containing a fluorine-based hydrocarbon containing 1,1,1,2-tetrafluoroethane (HFC-134a) into contact with at least one zeolite selected from the group consisting of chabazite zeolite, mordenite zeolite, beta zeolite, and zeolite Y to remove an impurity contained in the fluorine-based hydrocarbon compound, to produce a composition having a moisture content of less than about 3 ppmwt, and having a 1,1,2,2-tetrafluoroethane (HFC-134) content of less than 3 ppmwt.

7. A composition containing a fluorine-based hydrocarbon compound,
wherein the fluorine-based hydrocarbon compound contains at least one compound selected from the group consisting of 1,1,1,2-tetrafluoroethane (HFC-134a), 1,1,1,2,2-pentafluoroethane (HFC-125), and 2,3,3,3-tetrafluoropropene (HFO-1234yf), and
wherein a 1,1,2,2-tetrafluoroethane (HFC-134) content is at least 0.1 ppmwt, and less than 3 ppmwt, and a moisture content is less than 3 ppmwt.

8. The composition according to claim 7, which is for use in etching gas, refrigerants, heat-transfer mediums, deposit gas, building blocks for organic synthesis, or cleaning gas.

* * * * *